United States Patent [19]

Shinomura et al.

[11] Patent Number: 5,249,577
[45] Date of Patent: Oct. 5, 1993

[54] ULTRASONOTOMOGRAPHY

[75] Inventors: Ryuuichi Shinomura, Higashimatsuyama; Hiroshi Kanda, Tokorozawa; Koji Tanabe, Kashiwa, all of Japan

[73] Assignee: Hitachi Medical Corporation, Japan

[21] Appl. No.: 889,236

[22] Filed: May 28, 1992

[30] Foreign Application Priority Data

May 28, 1991 [JP] Japan .................................. 3-123318

[51] Int. Cl.$^5$ .............................................. A61B 8/06
[52] U.S. Cl. ........................ 128/660.05; 128/661.01; 128/661.09; 128/660.07; 73/625; 73/626
[58] Field of Search ...................... 128/660.01, 660.05, 128/660.06, 660.07, 661/01, 661.07, 661.08, 661.09; 73/861.25, 625, 626

[56] References Cited

U.S. PATENT DOCUMENTS

| | | | |
|---|---|---|---|
| 4,628,738 | 12/1986 | Burckhardt et al. | 128/661.01 |
| 4,873,985 | 10/1989 | Nakajima | 128/661.09 |
| 5,014,710 | 5/1991 | Maslak et al. | 128/660.05 |
| 5,060,651 | 10/1991 | Kondo et al. | 128/661.01 |
| 5,148,808 | 9/1992 | Satake | 128/660.05 |

FOREIGN PATENT DOCUMENTS

| | | | |
|---|---|---|---|
| 624988 | 2/1987 | Japan | 128/661.09 |
| 3-158144 | 8/1991 | Japan | 128/661.09 |

OTHER PUBLICATIONS

"Ultrasonic B-Scanner with multi-line array", by D. Hassler, D. Hanig and R. Schwarz, Medical Division Seimens, Ultrasonic Image 4, pp. 32-43, 1982.

Primary Examiner—William E. Kamm
Assistant Examiner—George Manuel
Attorney, Agent, or Firm—Antonelli, Terry, Stout & Kraus

[57] ABSTRACT

In ultrasonotomography, ultrasonic transducers are divided in the scanning direction and in a direction (elevation direction) orthogonal to the scanning direction and by changing the aperture in the elevation direction through focus in elevation direction, a tomogram and a Doppler signal of a blood flow can be obtained and displayed two-dimensionally. Doppler data is obtained by effecting slight angle scan of the ultrasonic beam mechanically or electronically in the elevation direction. Data pieces for the same raster of a plurality of Doppler data pieces obtained through the slight angle scan in the elevation direction are added-/averaged or added to improve the S/N ration. By effecting the slight angle scan of the ultrasonic beam in the elevation direction orthogonal to a tomogram plane, a vessel at a position deviant form the tomogram plane can be found. Also, by virtue of the variable aperture in elevation direction and the function of focus in elevation direction, the resolution of tomogram in the orthogonal direction can be improved to promote the intensity of signal. In addition, by adding/averaging or adding blood flow signals, the S/N ratio can be improved.

24 Claims, 3 Drawing Sheets

ULTRASONOTOMOGRAPHY

BACKGROUND OF THE INVENTION

The present invention relates to ultrasonotomography based on a Doppler signal from an object to be examined and more particularly to ultrasonotomography suitable for improving the performance of an ultrasonic diagnostic apparatus.

When an ultrasonic beam is applied at an incident angle to a blood flow inside a human body, the frequency of an ultrasonic wave reflected from the blood flow is shifted in accordance with velocity of the blood flow and a Doppler signal can be obtained. Thus, the blood flow velocity can be determined from this Doppler signal. Conventionally, in an ultrasonic diagnostic apparatus in which a Doppler signal is obtained to display a blood flow two-dimensionally, a blood flow in a tomogram plane from which a two-dimensional tomogram is obtained is measured and displayed. More particularly, where the array direction (azimuth direction) of transducers of a probe is y axis and a direction (elevation direction) orthogonal to the azimuth direction is x axis, focusing is effected in general in the elevation direction by means of a fixed lens (acoustic lens of fixed focus) and an ultrasonic beam is scanned in only the azimuth direction, whereby tomogram and Doppler data are obtained through scan in only the azimuth direction. One-dimensional electronic scan or mechanical scan is permitted by in order to effect two-dimensional scan, the operator manually moves a probe by changing the angle relative to x-axis direction to scan an ultrasonic beam broadly. Variable aperture in elevation direction and focus in elevation direction necessary for making a beam small in the x-axis direction have already been discussed in, for example, Ultrasonic B-scanner with multi-line array by D. Hassler, D. Honig and R. Schwarz, Medical division Siemens, Ultrasonic Imaging 4, pp. 32–43, 1982. Further, a method of applying this technique to obtaining Doppler data is described in JP-A-3-158144. Also, beam scan in the x-axis (elevation direction) is disclosed in, for example, JP-B-62-4988.

SUMMARY OF THE INVENTION

In the above prior art, when the diameter of an ultrasonic beam is larger than that of a vessel, resulting in degraded resolution, the S/N ratio of a Doppler signal of a blood flow is degraded. To overcome this problem, the ultrasonic beam is restricted in the azimuth direction by using the variable aperture and variable focusing. In the elevation direction, however, focusing is effected by means of an acoustic lens of fixed focusing point and if the ultrasonic beam in the elevation direction is thick, it is affected by a soft tissue and disadvantageously the S/N ratio of a Doppler signal is degraded. In addition, the prior art fails to take into consideration scanning of a Doppler beam standing for an ultrasonic beam for obtaining a Doppler signal in the x-axis (elevation) direction and a signal data processing method which uses a signal int eh x-axis (elevation) direction to measure a Doppler signal at a high S/N ratio, having difficulties in displaying a thin vessel outside the ultrasonic beam.

The present invention contemplates elimination of the above problems and its object is to provide an ultrasonotomographic method which uses an ultrasonic diagnostic apparatus having a variable aperture in elevation direction and the function of focus in elevation direction to provide a slightly sector scanned ultrasonic beam even in the elevation direction in order that a vessel outside the ultrasonic beam, undetectable with the prior art, can be found out with ease, thereby finding suitability to improving the S/N ratio of measured data.

According to the invention, to accomplish the above object, an ultrasonotomographic method for measuring and displaying a tomogram signal of an object to be examined and a Doppler signal of a blood flow by using an ultrasonic probe having, on a transmission/reception plane of an ultrasonic beam, a plurality of ultrasonic transducers arrayed in a first axis direction (azimuth direction) standing for a scan direction of the ultrasonic beam and a plurality of ultrasonic transducers arrayed in a second axis direction (elevation direction) orthogonal to the first axis direction, comprises the steps of: (a) changing the aperture for transmission and/or reception of the ultrasonic beam in the second axis direction, (b) obtaining a tomogram by effecting transmission/reception of the ultrasonic beam plural times in an angular direction substantially perpendicular to the second axis direction, (c) obtaining a plurality of Doppler signals by effecting transmission/reception of the ultrasonic beam plural times in angular directions making a plurality of different angles to the second axis direction on a plane which the tomogram is obtained, is substantially parallel to the second axis direction and contains the normal direction of the aperture portion on the transmission/reception plane, (d) performing each of the steps (a) and (c) by sequentially scanning the ultrasonic beam in the first axis direction, and (e) displaying the tomogram of the object to be examined and the plurality of Doppler signals in superimposed fashion.

The ultrasonotomography according to the invention also comprises obtaining a plurality of Doppler signals by effecting transmission/reception of the ultrasonic beam plural times in angular directions making a plurality of different angles to the second axis direction on a plane which is substantially perpendicular to a plane on which the tomogram is obtained, is substantially parallel to the second axis direction and contains the normal direction of the aperture portion on the transmission/reception plane, and adding/averaging or adding the plurality of Doppler signals to provide Doppler data.

The ultrasonotomography according to the invention also comprises obtaining a plurality of Doppler signals by effecting transmission/reception of the ultrasonic beam plural times in angular directions making a plurality of different angles to the second axis direction on a plane which is substantially perpendicular to a plane on which the tomogram is obtained, is substantially parallel to the second axis direction and contains the normal direction of the aperture portion on the transmission/reception plane, and displaying the plurality of Doppler corresponding to each direction of transmission/reception of the ultrasonic beam.

More specifically, the ultrasonotomography according to the invention comprises dividing ultrasonic transducers in the scanning direction and in a direction (elevation direction) orthogonal to the scanning direction and obtaining a tomogram and a Doppler signal of a blood flow by changing the aperture desirably in the elevation direction through focus in elevation direction and displaying them two-dimensionally, and obtaining Doppler data by effecting slight angle scan of the ultrasonic beam mechanically or electronically in the elevation direction.

The ultrasonotomography according to the invention also comprises adding/averaging or adding data pieces for the same raster of a plurality of Doppler data pieces obtained through the slight angle scan in the elevation direction to measure a Doppler signal at a high S/N ratio and display the Doppler signal.

In the present invention, by effecting the slight angle scan of the ultrasonic beam in the elevation direction orthogonal to a tomogram plane, a vessel at a position deviant from the tomogram plane can be found. Also, by virtue of the variable aperture in elevation direction and the function of focus in elevation direction, the resolution of tomogram in the orthogonal direction can be improved to promote the intensity of signal and besides by adding/averaging or adding blood flow signals, the S/N ratio can be improved.

DESCRIPTION OF THE PREFERRED EMBODIMENTS

An embodiment of the invention will no be described with reference to the accompanying drawings.

Figure 2:
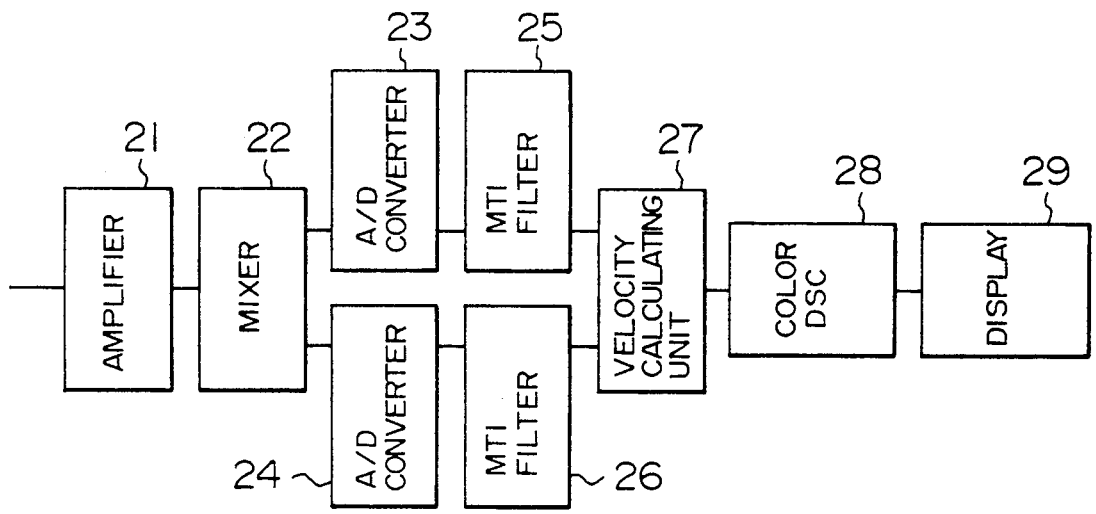
FIG. 2 is a block diagram showing the construction of an ultrasonic diagnostic apparatus to which ultrasonotomography of the invention is applied.

In FIG. 2, reference numeral 21 designates an amplifier, 22 a mixing circuit, 23 and 24 A/D (analog to digital) converters, 25 and 26 MTI (moving target indication) filters, 27 a velocity calculating unit, 28 a color DSC (digital scan converter) and 29 a display.

With the above construction, a received Doppler signal is amplified and mixed with a 90° dephased signal by means of the amplifier 21 and then converted into a digital signal by the A/D converter 23 or 24. Data received during one round preceeding transmission is subtracted from the digital signal by means of the MTI filter 25 or 26 to remove a signal produced from a still portion (clatter signal), blood flow velocity and the like factors are calculated by the velocity calculating unit 27, and the direction, velocity and dispersion of a blood flow are indicated in color by the color DSC 28 and displayed on the display 29.

Figure 1:
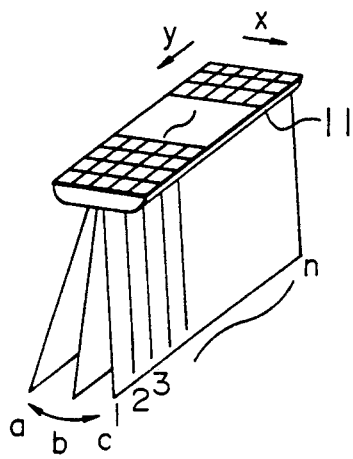
FIG. 1 is a diagram for explaining an embodiment of a method for scan in the x axis direction according to the invention.

An ultrasonic beam is scanned in a manner as shown in FIG. 1 to obtain a Doppler signal. For simplicity of explanation, the scanning method shown is based on a linear array probe. In FIG. 1, reference numeral 11 designates array transducers for generation of an ultrasonic wave, and y-axis direction corresponds to scanning direction (azimuth direction) and x-axis direction corresponds to orthogonal direction (elevation direction) to the scanning direction. The array transducers may be constructed by dividing a piezoelectrical material in y-axis and x-axis directions or by dividing a piezoelectrical material in the y-axis (azimuth) direction and dividing an electrode in the x-axis (elevation) direction. The sequence of scanning of an ultrasonic beam in the y-axis direction is indicated by 1 to n.

In the present embodiment, slight angle scan in the x-axis direction is effected by scanning a variable aperture in elevation direction and a variable focusing probe in elevation direction mechanically or through electronical scanning under varying conditions for variable focus in elevation direction. FIG. 1 shows the behavior of sector scan based on slight angle scan in three angular directions a, b and c.

Figure 3:
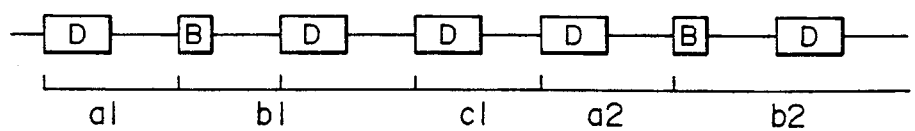
FIG. 3 is a diagram for explaining an embodiment of basic, data obtaining sequence according to the invention.

The basic sequence of obtaining data in this scan is shown in FIG. 3.

In FIG. 3, D represents obtaining the Doppler data and B represents obtaining the tomogram data. Numerals suffixed to a, b and c indicate the sequence of scanning in the y-axis direction shown in FIG. 1.

In this case, Doppler data D and tomogram data B are obtained in a front angular direction b of a scanning plane which is substantially perpendicular to the x-axis direction of the array transducers 11, Doppler data is obtained in angular directions a and b of scanning planes which are inclined relative to the x-axis direction of the array transducers 11, and the thus obtained Doppler data pieces are simultaneously superimposed on the tomogram data so as to be displayed. Thus, in the basic sequence, data is obtained in the order of Doppler data in a1, tomogram data in b1, Doppler data in b1, Doppler data in c1, Doppler data in a2, tomogram data in b2, Doppler data in b2 and Doppler data in c2.

Figure 4:
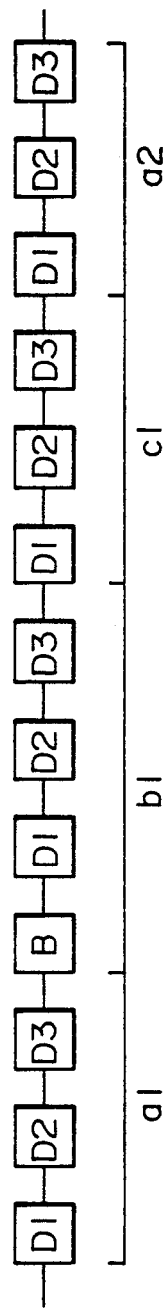
FIG. 4 is a diagram for explaining an embodiment of data obtaining sequence through addition/averaging or addition according to the invention.

The Doppler data pieces are added/averaged or added to improve quality of image and S/N ratio in a manner to be described below. FIG. 4 is a diagram for explaining an embodiment of the data obtaining sequence based on addition/averaging or addition according to the invention and FIG. 5 is a diagram for explaining an embodiment of the data obtaining sequence based on the MTI filter.

In the present embodiment, data pieces obtained in the angular directions a, b and c shown in FIG. 1 are added/averaged or added in accordance with the sequence shown in FIG. 4. For example, when obtaining data in a1, a plurality of Doppler data pieces, for example, three Doppler data pieces D1, D2 and D3 are obtained in order to improve the S/N (signal to noise) ratio. In a similar way, data in b1 and data in c1 are obtained in this order and the thus obtained data pieces are added/averaged or added by means of the velocity calculating unit 27. In an alternative method, data pieces obtained in each of the angular directions a, b and c are added/averaged or added and superimposed on each other for display. In this case, even when Doppler data is present in any one of the angular directions a, b and c alone, images of high quality can be displayed.

Figure 5:
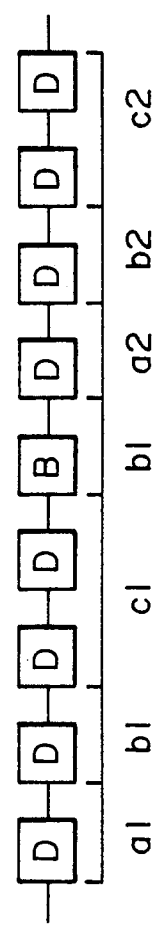
FIG. 5 is a diagram for explaining an embodiment of data obtaining sequence by means of an MTI filter according to the invention.

In case where the MTI filter 25 is applied to rasters in the angular directions a, b and c, the sequence shown in FIG. 5 is used. For example, the MTI filter 25 is applied to Doppler data obtained in the order of a1, b1 and c1, tomogram data in b1 is then obtained and subsequently Doppler data and tomogram data in a2, b2 and c2 are obtained in a similar way. When obtaining data in each of the angular positions a1, b1 and c1, a plurality of Doppler data pieces, for example, three Doppler data pieces D1, D2 and D3 are obtained and added-/averaged or added in order to improve the S/N (signal to noise) ratio.

Figure 6:
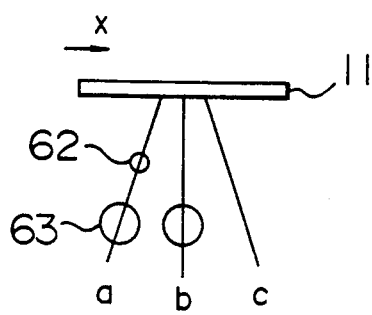
FIG. 6 is a diagram for explaining an embodiment of a method for angle setting upon scan in the x axis direction according to the invention.

Angle setting to be done when the slight angle scan is effected in the x-axis direction will now be described. FIG. 6 is a diagram for explaining an embodiment of a method for angle setting upon the x-axis direction scan according to the invention. In FIG. 6, reference numerals 62 and 63 designate vessels of which the vessel 62 stands for a thin vessel undetectable by scan in the angular direction b alone.

In the present embodiment, by performing scan in the angular directions a and c in addition to the conventional ordinary scan (scan in the angular direction b), data of the vessel 62 can also be obtained which cannot be obtained in the angular direction b. By performing sector scan through the slight angle in this manner, a blood flow can be obtained in the angular direction a and displayed in color. In this case, the angle is determined by vessel diameter r and depth z and may be related to them by "slight angle $\theta = \arctan(r/z)$".

The range of scan of an ultrasonic beam can be set automatically by using the intensity (strong or weak) of a blood flow signal or manually by using a fixed value inputted by the operator in advance. Specifically, on the assumption that relative to a vessel displayed through the ordinary scan, a different vessel having the same diameter as that vessel lies in the x-axis direction, the ultrasonic beam is further scanned in the x-axis direction to provide a display or an empirical value of scan range depending on diagnosis and an object to be displayed is inputted by the operator and a new value is inputted each time the examination object changes.

Doppler signals can be produced from the vessel 63 shown in FIG. 6 by using rasters in the angular directions a and b. In this case, by adding/averaging or adding the Doppler signals within a range of pixels represented in terms of the depth direction, the S/N ratio can be improved.

Further, it is assumed that the number of repetitive transmissions for obtaining Dopper data of one raster when the sector scan is not effected in the x-axis (elevation) direction is N. Then, if the sector scan is effected in the x-axis direction under the same condition, the frame rate is reduced to about ⅓ in the present embodiment and therefore, by making the number of repetitive transmissions for obtaining Doppler data of one raster equal to N/3, the frame rate can be kept to be substantially constant.

Figure 7:
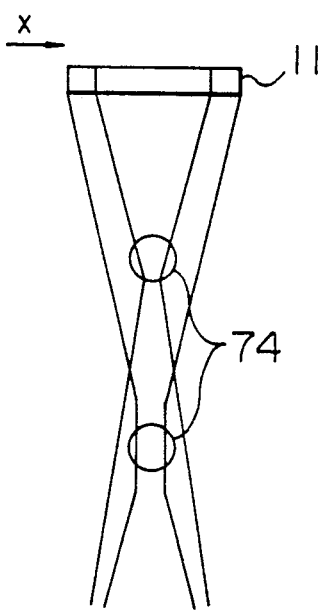
FIG. 7 is a diagram for explaining an embodiment of variable aperture in elevation direction according to the invention.

Variation of aperture in elevation direction in the present embodiment will now be described. FIG. 7 is a diagram for explaining an embodiment of variable aperture in elevation direction according to the invention. In FIG. 7, reference numeral 74 designates a vessel. In the present embodiment, by varying the aperture in the x-axis direction, a sharp beam is formed to draw thinner vessels. For example, when obtaining data at a short distance, the azimuth resolution at the short distance can be improved by making the aperture small in the x-axis direction of the array transducers, so that a vessel 74 at the short distance can be drawn. With the small aperture, however, a vessel 74 at a medium distance is buried in the ultrasonic beam and cannot be drawn. Accordingly, the aperture in the x-direction of the array transducers is enlarged to permit the vessel 74 at the medium distance as shown in FIG. 7 to be drawn. The operation of varying the aperture in the x-axis direction may be effected during only reception or during both transmission and reception. A similar effect can be attained by varying the focal position in the direction of depth of the examination object.

Figure 8:
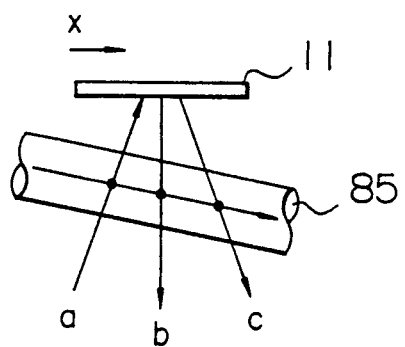
FIG. 8 is a diagram for explaining an embodiment of a method for detection of the blood flow direction according to the invention.

Detection of directivity of a blood flow will now be described. FIG. 8 is a diagram for explaining an embodiment of a method for detection of blood flow direction according to the invention. In FIG. 8, reference numeral 85 designates a vessel and the direction of a blood flow is indicated by arrow. For example, when data on different rasters are superimposed on each other without being subjected to addition/averaging or addition, the direction of a blood flow will be displayed oppositely in some case. In FIG. 8, it is decided by an ultrasonic beam a that the blood flow approaches the ultrasonic beam, and a display is effected in red. However, it is decided by an ultrasonic beam c that the blood flow departs from the ultrasonic beam and a display is effected in blue. In this manner, the direction of even the same blood flow is sometimes decided oppositely. The same result of decision of direction is obtained for the ultrasonic beam c and an ultrasonic beam b. Therefore, by adding/averaging or adding data pieces within the same pixel, the correct direction can be displayed. For example, when the blood flow is parallel to the array transducers 11, data pieces will be collapsed through addition/averaging but they may be confirmed if data on each raster of each of the angular direction a, b and c is displayed on time series basis. Data pieces may be added at the same timing on raster in the x-direction or at a constant distance from the surface.

In order for the user to perform the scan in the x-axis direction, a scanning method can be selected which adopts, for example, a broad scan mode in the x-axis direction wherein an ultrasonic beam is transmitted and received within a wide angular range covering a direction substantially perpendicular to the x-axis direction and a plurality of directions inclined relative to the x-axis direction, and effects the sector scan in the x-axis direction by using the broad scan mode. Alternatively, a scanning method can be employed in which contact of an ultrasonic probe to a human body is detected automatically and during only a predetermined interval of time following the detection, the broad scan mode is carried out automatically. Advantageously, through the above scanning methods, the blood flow can be displayed easily and an approximate position of the blood flow can be detected. For detection and display of the approximate position of the blood flow, a method may also be employed in which Doppler data and tomogram data are both obtained and displayed through sector scan in the x-axis direction in the broad scan mode. If the scanning direction of an ultrasonic beam in the x-axis direction useful for diagnosis exists, this scanning direction in the x-axis direction can be fixed and the ultrasonic beam can be scanned in the y-axis direction to obtain Doppler data and tomogram. In this case, the scanning direction in the x-axis direction may be fixed by the user or it may be set automatically in accordance with the intensity (strong or weak) of the Doppler data (blood flow signal). For example, the intensity of the Doppler data (blood flow signal) may be decided automatically and the direction of transmission/reception of an ultrasonic beam in the x-axis direction may be so fixed as to lie in a direction in which the maximum intensity of the Doppler data is obtained.

While the present embodiment has been described as using the linear array probe, similar effects may be obtained with an electronically scanning convex array probe or a phased array probe.

We claim:

1. An ultrasonotomographic method for measuring and displaying tomogram signals of an object to be examined and Doppler signals of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining tomogram signals and Doppler signals by effecting transmission/reception of the ultrasonic beam plural times in an angular direction substantially perpendicular to said second axis direction;
   (c) obtaining a plurality of Doppler signals by effecting transmission/reception of the ultrasonic beam plural times in angular directions making a plurality of different angles to said second axis direction in an elevation plane;
   (d) performing each of the steps (a) to (c) by sequentially scanning the ultrasonic beam in said first axis direction; and
   (e) displaying said tomogram of said object to be examined and said plurality of Doppler signals in superimposed fashion.

2. An ultrasonotomographic method according to claim 1 comprising obtaining a plurality of Doppler signals by effecting transmission/reaction of the ultrasonic beam plural times in angular directions making a plurality of different angles to said second axis direction on said elevation plane, and adding/averaging or adding said plurality of Doppler signals to provide Doppler data.

3. A method according to claim 2, wherein said elevation plane is a plane on which said tomogram is obtained, is substantially parallel to said second axis direction and contains the normal direction of the aperture portion on said transmission/reception plane.

4. An ultrasonotomographic method according to claim 1 comprising obtaining a plurality of Doppler signals by effecting transmission/reception of the ultrasonic beam plural times in angular directions making a plurality of different angles to said second axis direction on said elevation plane, and displaying said plurality of Doppler signals on time series basis on the same raster corresponding to each direction of transmission/reception of the ultrasonic beam.

5. A method according to claim 4, wherein said elevation plane is a plane which said tomogram is obtained, is substantially parallel to said second axis direction and contains the normal direction of the aperture portion on said transmission/reception plane.

6. A method according to claim 1, wherein said elevation plane is a plane on which said tomogram is obtained, is substantially parallel to said second axis direction and contains the normal direction of the aperture portion on aid transmission/reception plane.

7. An ultrasonotomographic method for measuring and displaying a tomogram signal of an object to be examined and a Doppler signal of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining a tomogram by effecting transmission/reception of the ultrasonic beam plural times in angular directions substantially perpendicular to said second axis direction;
   (c) obtaining a plurality of Doppler signals by effecting transmission/reception of the ultrasonic beam plural times in angular directions making a plurality of different angles to said second axis direction on a plane which is substantially perpendicular to a plane on which said tomogram is obtained, is substantially parallel to said second axis direction and contains the normal direction of the aperture portion on said transmission/reception plane;
   (d) performing each of the steps (a) to (c) by sequentially scanning the ultrasonic beam in said first axis direction;
   (e) displaying said tomogram of said object to be examined and said plurality of Doppler signals in superimposed fashion; an
   (f) detecting contacting of said ultrasonic probe to said object to be examined, and automatically scanning the ultrasonic beam in said second axis direction during a predetermined interval of time following the contacting to detect an approximate position of a blood flow.

8. An ultrasonotomographic method for measuring and displaying tomogram signals of an object to be examined and Doppler signals of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining tomogram signals by effecting transmission/reception of the ultrasonic beam plural times in angular directions substantially perpendicular to said second axis direction;
   (c) obtaining a plurality of Doppler signals by effecting transmission/reception of the ultrasonic beam plural times in an angular direction making a plurality of different angles to said second axis direction in an elevation plane;
   (d) performing each of the steps (a) to (c) by sequentially scanning the ultrasonic beam in said first axis direction;
   (e) displaying said tomogram of said object to be examined and said plurality of Doppler signals in superimposed fashion; and
   (f) obtaining tomogram signals and a Doppler signal in said first axis direction by fixing the angular direction of transmission/reception of the ultrasonic beam in said second axis direction in said elevation plane to a predetermined angular direction.

9. An ultrasonotomographic method according to claim 8, wherein the predetermined angular direction is an angular direction in which the intensity of the Doppler signal is maximized.

10. An ultrasonotomographic method for measuring and displaying tomogram signals of an object to be examined and Doppler signals of a blood flow by using an ultrasonic probe having, on a transmission/reception plane of an ultrasonic beam, a plurality of ultrasonic transducers arrayed in a first axis direction of a scan direction of an ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining tomogram signals and Doppler signals by effecting transmission/reception of ultrasonic beam plural times in an angular direction substantially perpendicular to said second axis direction;
   (c) obtaining a plurality of Doppler signals by effecting transmission/reception of the ultrasonic beam plural times in angular directions making a plurality of different angles to aid second axis direction in an elevation plane and averaging or adding said plurality of Doppler signals to provide Doppler data for said each angular direction;
   (d) performing each of the steps (a) to (c) by sequentially scanning the ultrasonic beam in said first axis direction; and
   (e) displaying said tomogram of said object to be examined and said plurality of Doppler signals in superimposed fashion.

11. An ultrasonotomographic method according to claim 10, further comprising the step of displaying said plurality of Doppler signals in superimposed relation with said tomogram on a time series basis on the same raster corresponding to each direction of transmission/reception of the ultrasonic beam.

12. A method according to claim 11, wherein said elevation plane is substantially perpendicular to a plane on which said tomogram is obtained, is substantially parallel to said second axis direction and contains the normal direction of the aperture portion on said transmission/reception plane.

13. A method according to claim 10, wherein said elevation plane is a plane which is substantially perpendicular to a plane on which said tomogram is obtained, is substantially parallel to said second axis direction and contains the normal direction of the aperture portion on said transmission/reception plane.

14. An ultrasonotomographic method for measuring and displaying a tomogram signals of an object to be examined and a Doppler signal of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining tomogram signals by effecting transmission/reception of the ultrasonic beam plural times in angular directions substantially perpendicular to said second axis direction;
   (c) obtaining a plurality of Doppler signals by effecting transmission/reception of the ultrasonic beam plural times in an angular direction making a plurality of different angles to said second axis direction in an elevation plane;
   (d) performing each of the steps (a) to (c) by sequentially scanning the ultrasonic beam in said first axis direction;
   (e) displaying said tomogram of said object to be examined and said plurality of Doppler signals in superimposed fashion; and
   (f) detecting contacting of said ultrasonic probe to said object to be examined, and automatically scanning the ultrasonic beam in said second axis direction during a predetermined interval of time following the contacting to detect an approximate position of a blood flow.

15. An ultrasonotomographic method for measuring and displaying a tomogram signals of an object to be examined and Doppler signal of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:
   (a) changing the aperture of transmission and/or reception of the ultrasonic beam in said second axis direction;
   (b) obtaining tomogram signals by effecting transmission/reception of the ultrasonic beam plural times in angular directions substantially perpendicular to said second axis direction;
   (c) obtaining a plurality of Doppler signals by effecting transmission/reception of the ultrasonic beam plural times in an angular direction making a plurality of different angles to said second axis direction in an elevation plane and averaging or adding said plurality of Doppler signals to obtain Doppler data;
   (d) performing each of the steps (a) to (c) by sequentially scanning the ultrasonic beam in said first axis direction;
   (e) displaying said tomogram of said object to be examined and said plurality of Doppler signals in superimposed fashion; and
   (f) obtaining tomogram signals and Doppler signals in said first axis direction by fixing the angular direction of transmission/reception of the ultrasonic beam plural times in said second axis direction to a predetermined angular direction in the elevation plane.

16. An ultrasonotomographic method according to claim 15, wherein the predetermined angular direction is an angular direction in which the intensity of the Doppler signal is maximized.

17. A method according to claim 15, wherein said elevation plane is substantially perpendicular to a plane on which said tomogram is obtained, is substantially parallel to said second axis direction and contains the normal direction of the aperture portion on said transmission/reception plane.

18. An ultrasonotomographic method for measuring an displaying tomogram signals of an object to be examined and Doppler signals of a blood flow by using an ultrasonic probe having, on a transmission/reception plane of an ultrasonic beam, a plurality of ultrasonic transducers arrayed in a first axis direction standing for a scan direction of the ultrasonic beam and a plurality of ultrasonic transducers arrayed in a second direction orthogonal to the first axis direction, comprising the steps of:

(a) changing the aperture of transmission and/or reception of the ultrasonic beam in said second axis direction;

(b) obtaining tomogram signals and Doppler signals by effecting transmission/reception of the ultrasonic beam plural times in an angular directions substantially perpendicular to said second axis direction in an elevation plane;

(c) obtaining a plurality of Doppler signals by effecting transmission/reception of the ultrasonic beam plural times in an angular direction making a plurality of different angles to said second axis direction in an elevation plane;

(d) performing each of the steps (a) to (c) by sequentially scanning the ultrasonic beam in said first axis direction;

(e) displaying said plurality of Doppler signals in superimposed relation with said tomogram on time series basis on the same raster corresponding to each direction of transmission/reception of the ultrasonic beam.

19. A method according to claim 18, wherein said elevation plane is substantially perpendicular to a plane on which said tomogram is obtained, is substantially parallel to said second axis direction and contains the normal direction of the aperture portion on said transmission/reception plane.

20. A method according to claim 19, wherein said plurality of Doppler signals are obtained in angular directions making a plurality of different angles to said second axis direction.

21. An ultrasonotographic method for measuring and displaying of tomogram signal of an object to be examined and of Doppler signal of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:

(a) changing the aperture of transmission and/or reception of the ultrasonic beam in said second axis direction;

(b) obtaining tomogram by effecting transmission/reception of the ultrasonic beam plural times in an angular direction substantially perpendicular to said second axis direction in an elevation plane;

(c) obtaining a plurality of Doppler signals by effecting transmission/reception of the ultrasonic beam plural times in an angular direction making a plurality of different angles to said second axis direction on a plane which is substantially perpendicular to a plane on which said tomogram is obtained, is substantially parallel to said second axis direction and contains the normal direction of the aperture portion on said transmission/reception plane;

(d) performing each of the steps (a) to (c) by sequentially scanning the ultrasonic beam in said first axis direction;

(e) displaying said plurality of Doppler signals obtained in angular directions making a plurality of different angles to said second axis direction on a plane which is substantially perpendicular to a plane on which said tomogram is obtained, is substantially parallel to said second axis direction and contains the normal direction of the aperture portion on said transmission/reception plane, in superimposed relation with said tomogram on time series basis on the same raster corresponding to each direction of transmission/reception of the ultrasonic beam; and (f) detecting contacting of said ultrasonic probe to said object to be examined, and automatically scanning the ultrasonic beam in said second axis direction during a predetermined interval of time following the contacting to detect an appropriate position of a blood flow.

22. An ultrasonotomographic method for measuring and displaying tomogram signals of an object to be examined and Doppler signals of a blood flow by using an ultrasonic probe having, on a transmission/reception plane of an ultrasonic beam, a plurality of ultrasonic transducers arrayed in a first axis direction of a scan direction of the ultrasonic beam and a plurality of ultrasonic transducers arrayed in a second direction orthogonal to the first axis direction, comprising the steps of:

(a) changing the aperture of transmission and/or reception of the ultrasonic beam in said second axis direction;

(b) obtaining tomogram signals and Doppler signals in said first axis direction plural times in said second axis direction;

(c) obtaining a plurality of Doppler signals by effecting transmission/reception of the ultrasonic beam plural times in a predetermined angular direction making a predetermined angle to said second axis direction in an elevation plane;

(d) performing each of the steps (a) to (c) by sequentially scanning the ultrasonic beam in said first axis direction;

(e) displaying said plurality of Doppler signals in superimposed relation with said tomogram on time series basis on a raster corresponding to each direction of transmission/reception of the ultrasonic beam; and (f) obtaining tomogram signals and Doppler signals in said first axis direction by fixing the angular direction of transmission/reception of the ultrasonic beam in said second axis direction to a predetermined angular direction.

23. An ultrasonotomographic method according to claim 22, wherein the predetermined angular direction is an angular direction in which the intensity of the Doppler signal is maximized.

24. A method according to claim 22, further comprising the step of detecting an approximate position of a blood flow by automatically scanning the ultrasonic beam in said second axis direction during a predetermined interval of time following the contacting after detecting contacting of said ultrasonic probe to said object to be examined.

* * * * *